United States Patent
Staack et al.

(10) Patent No.: US 8,920,361 B2
(45) Date of Patent: Dec. 30, 2014

(54) PLASMA TREATMENT AND PLASMA ENHANCED CHEMICAL VAPOR DEPOSITION ONTO TEMPERATURE SENSITIVE BIOLOGICAL MATERIALS

(75) Inventors: David Staack, College Station, TX (US); Tsung-Chan Tsai, College Station, TX (US)

(73) Assignee: The Texas A&M University System, College Station, TX (US)

( * ) Notice: Subject to any disclaimer, the term of this patent is extended or adjusted under 35 U.S.C. 154(b) by 217 days.

(21) Appl. No.: 13/440,615

(22) Filed: Apr. 5, 2012

(65) Prior Publication Data

US 2012/0259272 A1    Oct. 11, 2012

Related U.S. Application Data

(60) Provisional application No. 61/471,766, filed on Apr. 5, 2011.

(51) Int. Cl.
| | | |
|---|---|---|
| *A61B 18/06* | (2006.01) | |
| *A61L 2/14* | (2006.01) | |
| *A61B 18/04* | (2006.01) | |
| *B05D 1/00* | (2006.01) | |

(52) U.S. Cl.
CPC ............... *A61L 2/14* (2013.01); *A61L 2202/11* (2013.01); *B05D 1/62* (2013.01); *A61B 18/042* (2013.01)
USPC ................................................ 604/24; 607/2

(58) Field of Classification Search
CPC ................... H05H 1/24; A61B 18/042; A61B 2018/00982; A61L 2/14; A61M 2202/0476
USPC .................................... 606/49; 607/2; 604/24
See application file for complete search history.

(56) References Cited

U.S. PATENT DOCUMENTS

| | | | |
|---|---|---|---|
| 2007/0292972 A1* | 12/2007 | Paulussen et al. | ............ 436/519 |
| 2008/0193745 A1* | 8/2008 | Jeong et al. | ................... 428/336 |
| 2009/0054896 A1 | 2/2009 | Fridman et al. | ................ 606/49 |
| 2012/0089084 A1* | 4/2012 | O'Keeffe et al. | ............... 604/24 |

FOREIGN PATENT DOCUMENTS

| | | | | |
|---|---|---|---|---|
| WO | WO 2010/009103 | 1/2010 | ............. A61B 18/00 |
| WO | WO 2010/107722 | 9/2010 | ................ B03C 3/74 |

OTHER PUBLICATIONS

D. Staack, "Plasma enhanced polymer film deposition onto inorganic, biological and living substrates at ambient conditions" NSF Proposal (Oct. 1, 2010).

(Continued)

*Primary Examiner* — Christopher D Koharski
*Assistant Examiner* — Michael Carey
(74) *Attorney, Agent, or Firm* — Wong, Cabello, Lutsch, Rutherford & Brucculeri, L.L.P.

(57) ABSTRACT

A method and apparatus for depositing a film on a biological substrate are provided. A plasma generation device includes a dielectric conduit and a high voltage electrode. The plasma generation device is placed in proximity to the biological substrate and a gas supply that includes a precursor material is directed through the dielectric conduit. An electric field generated by the potential difference between the high voltage electrode and the biological substrate ionizes at least a portion of the gas supply and causes plasma to emanate from the dielectric conduit and contact the biological substrate. The plasma induces a reaction of the precursor material to form a film that is deposited on the biological substrate.

23 Claims, 5 Drawing Sheets

(56) References Cited

OTHER PUBLICATIONS

T.-C. Tsai and D. Staack, "Low-temperature Polymer Deposition in Ambient Air Using a Floating-electrode Dielectric Barrier Discharge Jet," Plasma Processes and Polymers, vol. 8, pp. 523-524 (Jun. 22, 2011).

T.-C. Tsai, J. Cho, Y.-K. Jo and D. Staack, "Sterilization and Inhibition of Bacteria Growth by Polymer Film Barriers Deposited Using a Floating-Electrode Dielectric Barrier Discharge Plasma Jet in Ambient Environment Conditions," ISPC 20 (Jul. 24-29, 2011).

* cited by examiner

PLASMA TREATMENT AND PLASMA ENHANCED CHEMICAL VAPOR DEPOSITION ONTO TEMPERATURE SENSITIVE BIOLOGICAL MATERIALS

CROSS REFERENCE TO RELATED APPLICATIONS

This application claims priority to U.S. Provisional Application Ser. No. 61/471,766, entitled "Plasma Treatment and Plasma Enhanced Chemical Vapor Deposition onto Temperature Sensitive Biological Materials," filed Apr. 5, 2011, the entire contents of which are incorporated herein by reference.

FIELD OF THE DISCLOSURE

This disclosure relates generally to a system and method for depositing films on a biological substrate. More specifically, but not by way of limitation, this disclosure is related to the utilization of plasma enhanced chemical vapor deposition as a mechanism to deposit a material on a biological substrate.

BACKGROUND

Plasma enhanced chemical vapor deposition (PECVD) is a low pressure materials deposition technique in which thin films with highly tailored properties and functionality can be deposited onto a substrate. PECVD is most widely used in the semiconductor industry for the deposition of silicon dioxide onto wafers containing metal layers and other temperature sensitive structures. Typically PECVD reactors operate at very low pressures (e.g., a fraction of a Torr). The plasma is necessarily non-equilibrium and non-thermal, with high energy electrons and neutral atoms at near ambient temperature. Through collisions, the high electron energy allows for the creation of the chemically reactive species which form the deposited film. The low neutral temperature prevents thermal damage of the substrate.

Over the past decade, advances in the understanding of non-equilibrium, 'cold', atmospheric pressure plasmas have led researchers to investigate the possibilities of atmospheric pressure PECVD. The main reasons for pursuing research in AP-PECVD were: 1) lower operating cost, due to the lack of expensive vacuum processing equipment; 2) higher deposition rates, due to the higher densities of operation; and 3) continuous processing, due to the relaxation of the requirement to process substrates in batch mode.

While most research in the area of AP-PECVD has focused on alternative methods to current low pressure processing techniques, such as SiO2 film deposition, the use of non-thermal plasmas for the treatment of living organisms is a recent and exciting field. Significant findings have been made in the sterilization of surfaces from bacteria based on exposure to plasma. More recently, plasma sterilization has been shown in animal and human studies. Non-thermal plasma has also been shown to enable tissue bonding through thermal coagulative bonding, chemical denaturing bonding, and blood coagulation bonding. Most of these applications of plasma to biological substrates have used gases consisting of mixtures of air with noble gases.

While several beneficial effects from the exposure of biological materials to non-thermal plasma have been noted, the interaction of reacting chemistries (beyond those of air's constituents) with biological surfaces and deposition onto living substrates has not yet been investigated. There is therefore a need in the art to develop a mechanism by which living substrates may be exposed to non-thermal plasma containing different chemical constituents and by which plasma-generated films may be deposited on these surfaces.

DETAILED DESCRIPTION

The following is a detailed description for carrying out embodiments of the invention. This description is not to be taken in a limiting sense, but is made merely for the purpose of illustrating the general principles of the example embodiments of the invention.

Application of PECVD to biological substrates must begin with the selection of an appropriate plasma source. As used herein, the term biological substrate refers to a surface of a living organism. An appropriate source must therefore be capable of operating at atmospheric pressure, in ambient air, and must enable film deposition at temperatures that are suitable for the biological substrate. One of the most well developed sources for thin film deposition is the atmospheric pressure plasma jet (APPJ), a radio frequency (13.6 MHz) capacitively coupled discharge operating in noble gases flows. However, APPJ systems typically run a bit hot, with high gas flow rates required to maintain low temperatures, and are susceptible to instabilities when high concentrations of impurities are introduced into the discharge. Typically, precursors are added in the afterglow of the discharge and most deposition studies have been of inorganic films. For application of PECVD to biological substrates, the deposited films will often be polymers in order to more closely resemble the biological substrate. In general, plasma polymerized films are firmly adhesive to various substrate surfaces, and their physical or chemical features are controllable by adjusting the parameters of discharge. Consequently, the APPJ system is not an optimal source for application of PECVD to biological substrates.

A known source for the deposition of plasma-polymerized films at low temperatures and atmospheric pressure is a dielectric barrier discharge (DBD) system with parallel-plate electrodes. While DBD systems enable the deposition of plasma-polymerized films at atmospheric pressure and suitable temperatures, the parallel-plate configuration of the electrodes limits their application in deposition on 3-D free-form biological substrates due to the small gap distance between the electrodes that is required for stable plasma generation. Therefore, the DBD system with parallel-plate electrodes is also not an optimal source for application of PECVD to biological substrates.

However, a variation on the DBD system utilizes a single powered electrode with the substrate serving as the second electrode. Termed a floating-electrode dielectric discharge barrier device (FE-DBD), this type of device is optimal for the deposition of films on a biological substrate as it enables deposition on various types of surfaces at long working distances and is capable of operating at atmospheric pressure in ambient air. Moreover, a FE-DBD device is particularly suitable for 3-D coating and local film deposition with low temperature due to its advantages of high plasma stability, efficient reaction chemistry and low power consumption.

Figure 1:
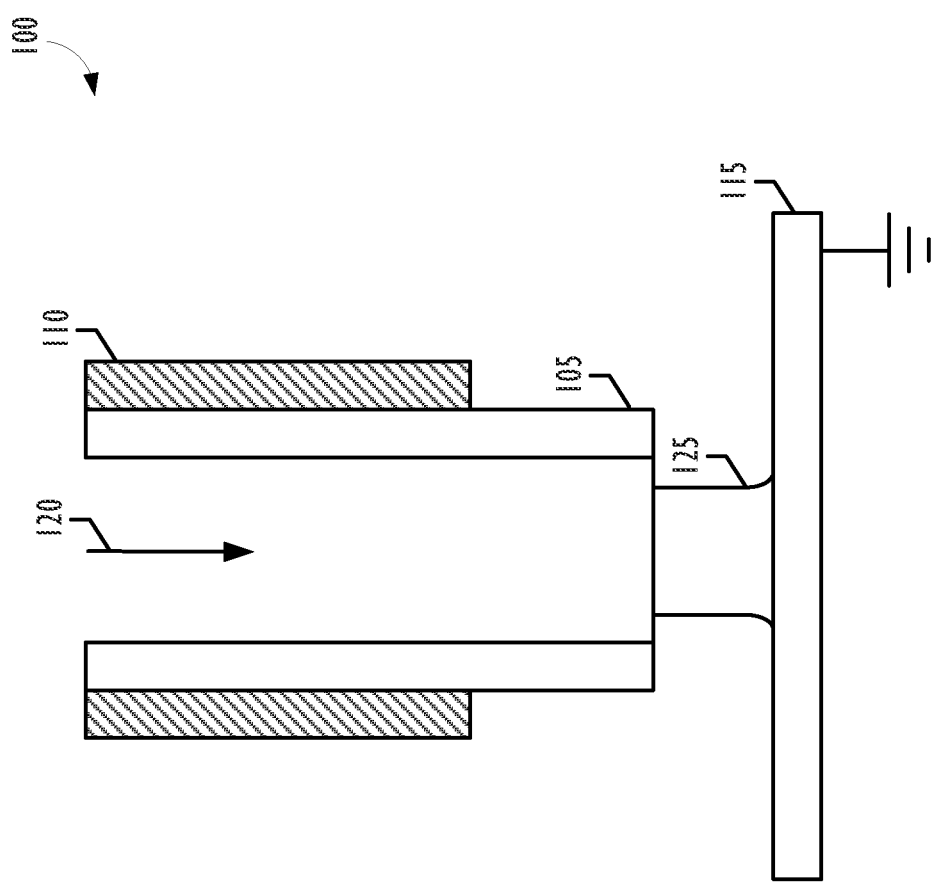
FIG. 1 is a cross-sectional view of the major components of a floating electrode dielectric barrier discharge (FE-DBD) plasma generation device.

A cross-sectional view of the major components of a FE-DBD device for the generation of non-thermal plasma in accordance with one embodiment of the disclosure is illustrated in FIG. 1. As illustrated, because the device employs a single powered electrode 110 with the substrate 115 serving as the ground electrode, the device 100 may be described as a floating-electrode dielectric barrier discharge (FE-DBD) device. In the illustrated plasma generation device 100, a dielectric conduit 105 is positioned between the high voltage electrode 110 and the substrate (i.e., the ground electrode) 115. The high voltage electrode 110 is coupled to a power supply configured to deliver an alternating voltage having a desired waveform and frequency. The substrate 115 is at a ground potential with respect to the high voltage electrode 110.

Supply gas is communicated within an interior passage of the dielectric conduit 105 in the direction indicated by the arrow 120. As the supply gas is passed through the dielectric conduit 105, the electric field generated by the potential difference between the high voltage electrode 110 and the substrate 115 induces the ionization of at least a portion of the supply gas wherein the bond between an electron and an atom is broken and the electron transitions from a ground state to an unbound state. The free moving electrons receive energy from the applied field and through collisions transfer that energy to the gas, furthering ionization, electronic excitation, vibrational excitation, the generation of heat and thus generating a non-thermal plasma. The non-thermal plasma emanates from the end of the dielectric conduit 105 in the form of a plasma jet 125 that impinges on the substrate 115. Although the device 100 has been described at a relatively high level, the device 100 will be described in greater detail below with respect to the instant disclosure. Moreover, additional details may be obtained by reference to International Application Number PCT/US2010/027376, filed Mar. 16, 2010, entitled "Tubular Floating Electrode Dielectric Barrier Discharge for Applications in Sterilization and Tissue Bonding," published as WO2010/017722 Sep. 23, 2010, the entire contents of which are incorporated herein by reference.

Figure 2:
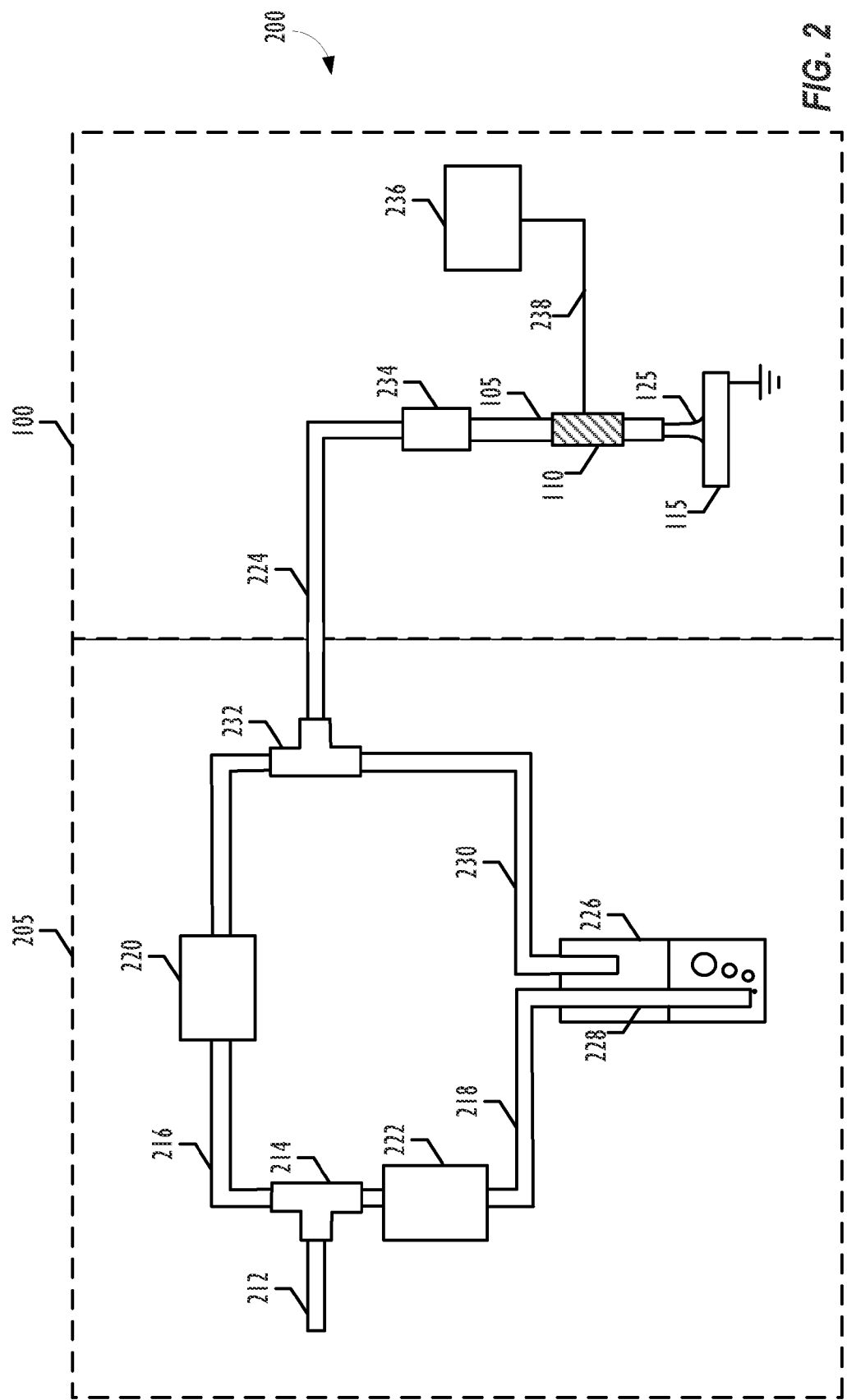
FIG. 2 is a block diagram illustrating the components of a system to introduce a precursor into a gas flow to a FE-DBD plasma generation device.

Referring to FIG. 2, a system 200 for introducing a precursor source into a gas flow for plasma generation is illustrated. The system 200 includes a gas feed system 205 and a FE-DBD device 100, which is essentially the same as that described above with respect to FIG. 1, FE-DBD device 100 is described in greater detail with respect to its application within system 200.

Gas feed system 205 includes various components for introducing a desired precursor into a gas flow for plasma generation. As an example, throughout the specification, the working gas is described as helium and the precursor is described as methyl methacrylate monomer (MMA). As will be understood by those of ordinary skill in the art, however, different working gas and precursor components may be employed. Helium gas supplied to gas introduction port 212 passes through a splitter 214, which separates the working gas flow 216 from the carrier gas flow 218. The carrier gas flow 218 is directed through a vessel 226. More specifically, the carrier gas flow 218 is directed into the vessel 226 (e.g., a bubbler) through a dip tube 228 that extends below a liquid level of MMA precursor in the vessel 226. In one embodiment, the vessel may be a glass container that is coupled to the dip tube 228 and the vapor tube 230. The liquid MMA monomer is vaporized by the helium carrier gas flow 218, and the vaporized MMA and helium exit the vessel through vapor tube 230. The working gas flow 216 and the carrier gas flow 230 (containing the helium/MMA mixture) are combined into the combined gas 224 flow at the mixing tee 232.

A working gas flow controller 220 operates in conjunction with a carrier gas flow controller 222 to maintain a constant combined gas 224 flow rate to the FE-DBD device 100. In one embodiment, both the working gas flow controller 220 and the carrier gas flow controller 222 are digital mass flow control devices. In one embodiment, the working gas flow controller 220 and the carrier gas flow controller 222 operate in conjunction to maintain a combined gas 224 flow rate of 3 slpm (standard liters per minute). In such an embodiment, the carrier gas flow rate may be set within a range of approximately 0.05 to 0.4 slpm to achieve a desired concentration of MMA precursor within the combined gas 224 flow. Typically, the concentration of MMA in the combined gas 224 flow will be maintained within a range of 100-5000 parts per million (ppm). It is important to maintain a desired concentration of precursor within the combined gas 224 flow. If the precursor concentration is too low, the desired interaction between the non-thermal plasma and the substrate (e.g., film deposition) will not be attainable, and, if the precursor concentration is too high, the ability to generate the non-thermal plasma will be destroyed. While the working gas flow controller 220 and the carrier gas flow controller 222 have been described as working in conjunction, it is to be understood that the controllers may operate independently but may be set by an operator such that a desired combined flow rate is achieved.

The combined gas 224 flow is introduced to the dielectric conduit 105 of the FE-DBD device 100 through a coupler 234. In one embodiment, the illustrated flow paths of the gas feed system 205 may be formed by tubing. In one embodiment, the tubing may be composed of glass or a suitable polymeric material. In a particular embodiment, the tubing connecting the mixing tee 232 to the coupler 234 may be formed from a flexible tubing material (such as PFA, PTFE, etc.) and may be of a length suitable to allow for convenient positioning of the FE-DBD device 100 with respect to the substrate 115. In one embodiment, the dielectric conduit is a borosilicate glass tube. In one embodiment, the glass tube may have a length of approximately 12 cm, an external diameter of approximately 0.25 inches, and an internal diameter of approximately 0.15 inches. The dielectric conduit 105, however, may be formed of any suitable dielectric material such as quartz, ceramic, plastics (e.g., teflon), porcelain, etc., and may be of any size suitable for the particular application. For example, the length of the dielectric conduit 105 may be extended to enable endoscopic procedures utilizing the disclosed system.

In the depicted embodiment, a high voltage electrode 110 fits tightly around the circumference of the dielectric conduit 105. In one embodiment, the high voltage electrode 110 may be composed of any suitable conductive component such as copper, aluminum, etc. In one embodiment, the high voltage electrode 110 is formed from metallic tubing and is positioned such that the dielectric conduit 105 protrudes from the downstream end of the high voltage electrode 110. In one embodiment, the high voltage electrode 110 has a length of 30 mm and is positioned such that the dielectric conduit 205 protrudes from the downstream end of the high voltage electrode 110 by a distance of approximately 15 mm. It will be understood that the described dimensions and positioning are provided to describe a particular implementation and should not be understood as limiting the scope of the disclosure in any manner. That is, the placement and dimensions of the described components may vary according to a desired functionality of the system 200.

The high voltage electrode 110 is connected to an AC high voltage power supply 236 by means of a conductor 238. In one embodiment, the power supply 236 may be configured to deliver an AC voltage having a sinusoidal waveform and a frequency ranging from 60 Hz to 120 kHz. This waveform may be operated at a duty cycle of approximately 5%-100% in order to manage the balance between gas heating and plasma generation. The duty cycle frequency may be less than or comparable to the driving waveform frequency. Such duty cycling may also be implemented by having multiple frequency components (60 Hz to 120 kHz) in the driving waveform. Therefore, the power supply may be configured to deliver an arbitrary voltage waveform to the high voltage electrode 110. The magnitude of the voltage provided by the power supply 236 is dependent upon the dimensions and positioning of the components of the FE-DBD device 100, the concentration of the precursor material in the combined gas 224 flow, the desired properties of the film deposited by the plasma generation process, and the positioning of the FE-DBD device with respect to the substrate 115. Generally, however, the voltage will have a magnitude of between 2 and 10 kV.

In one embodiment, the downstream end of the dielectric conduit 105 may be positioned between 1 mm and 3 cm away from the substrate 115, depending upon the particular implementation. As the combined gas 224 is passed through the dielectric conduit 105, the electric field generated by the potential difference between the high voltage electrode 110 and the substrate 115 induces the ionization of at least a portion of the combined gas 224 wherein the bond between an electron and an atom is broken and the electron transitions from a ground state to an excited state. When this occurs, a plasma discharge 125 extends downstream from the high voltage electrode 110 towards the substrate surface 115. Therefore, the FE-DBD device 100 allows active plasma 125 to be generated in the vicinity of a biological substrate 115 at low temperature, atmospheric pressure, and in ambient conditions.

The generation of plasma initiates a reaction of the precursor material within the plasma discharge 125. For example, based on the presence of MMA precursor within the combined gas 224 flow, a polymerization reaction is initiated. In plasma polymerization, the transformation of monomers into high molecular weight molecules (polymers) occurs with the assistance of the energetic plasma species such as electrons, ions, and radicals. Plasma polymerization is chemically different from conventional polymerization, which involves radicals and ions. In many cases, polymers formed by plasma polymerization have different chemical compositions as well as chemical and physical properties from those formed by conventional polymerization, even if the same monomers are used in plasma polymerization and conventional radical or ionic polymerization. This uniqueness results from the reaction mechanism of the polymer-forming process. Polymer formation in plasma polymerization encompasses plasma activation of monomers to radicals, recombination of the formed radicals, and reactivation of the recombined molecules. Plasma polymers do not comprise repeating monomer units, but instead complicated units containing cross-linked, fragmented, and rearranged units from the monomers. In most cases, plasma polymers have a higher elastic modulus and do not exhibit a distinct glass transition temperature.

The plasma polymerization process of the MMA monomer results in the deposition of poly(methyl methacrylate) (PMMA) film on the substrate 115. PMMA is known to be a biocompatible material that is currently used in artificial bones and exhibits strong adhesion to biological substrates. Therefore, in an interesting application, the disclosed deposition process may be utilized to form a highly sterile and conformal bandage. For example, an infected wound (like a burn or ulcer) could be sterilized and coated with a polymeric film in accordance with the disclosed film deposition process. The thin film would conform to the wound and could prevent further infection. Furthermore, by controlling system parameters, the properties of the deposited film could be controlled. For example, the system parameters could be adjusted to achieve a desired porosity or biodegradability of the film or to provide cell growth promoters or antimicrobial compounds doped into the film. This bandage deposition process could build upon the plasma's unique sterilization capabilities, combining the sterilization and deposition steps.

Figure 3:
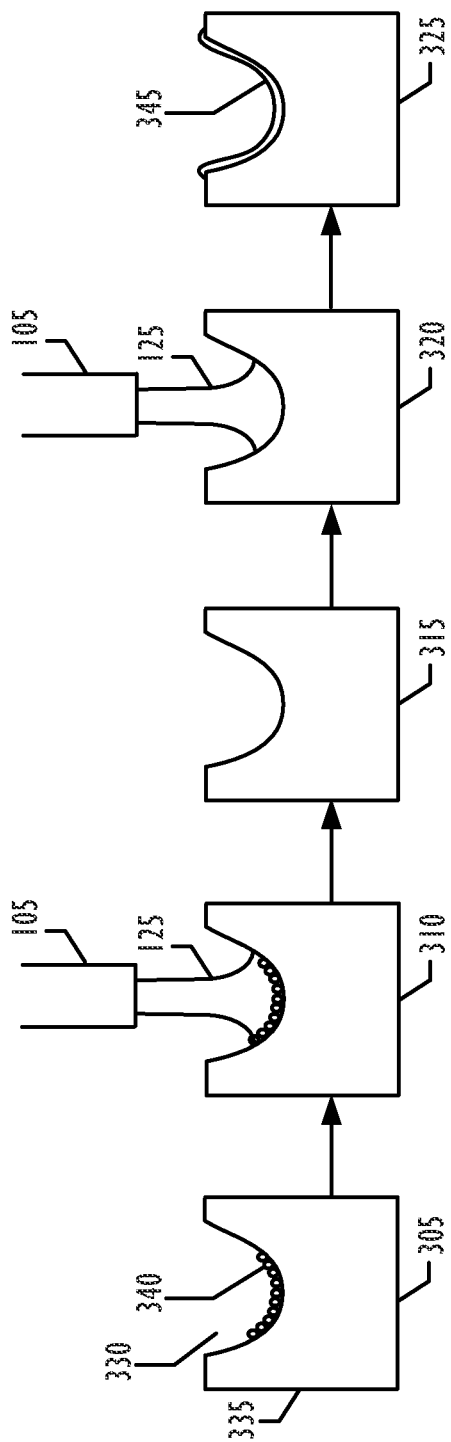
FIG. 3 illustrates the sterilization and deposition of a polymeric film bandage on a wound based on exposure of the wound to a plasma jet containing a desired polymer precursor.

Referring to FIG. 3, the deposition of a polymeric film bandage on a biological substrate is illustrated. At 305, a wound 330 in skin tissue 335 is infected with bacteria 340. At 310, the wound 330 is exposed to plasma 125 emitted from the FE-DBD device 100. In the depicted embodiment, the skin tissue 335 serves as the substrate 115 (i.e., the ground electrode in the floating electrode system). In one embodiment, the combined gas 224 flow to generate the plasma 125 at 310 may be formed without the polymeric precursor. That is, the carrier gas flow 218 may be blocked such that only the working gas flow 216 (e.g., containing only helium) may be transferred to the dielectric conduit 105 of the FE-DBD device 100. In such an embodiment, flow controllers 220 and 222 may be pre-programmed to provide a predetermined working gas 216 flow rate with no carrier gas 218 flow for a certain duration prior to introducing the precursor into the combined gas 224 flow by increasing the carrier gas 218 flow rate. At 315, exposure of the wound 330 to plasma 125 sterilizes the wound 330, killing the bacteria 340. At 320, the wound is again exposed to plasma 125. At 320, the combined gas 224 flow to the FE-DBD device 100 includes the precursor. As such, the generation of the plasma 125 initiates a plasma polymerization reaction by which a polymeric film 345 is deposited over the wound 330. In one embodiment, the precursor material may be MMA and the polymeric film 345 may be PMMA. As illustrated, the polymeric film 345 conforms to the shape of the wound and strongly adheres to the skin tissue 335. As such, exposure of the infected wound 330 to the plasma treatment sterilizes the wound 330 and generates a polymeric film bandage that provides a protective barrier to prevent subsequent infection of the wound 330. Although the depicted embodiment illustrates the process as if sterilization (310) and film deposition (320) occur in series, sterilization and film deposition may actually occur simultaneously as a result of a single exposure of the wound 330 to the plasma 125. In fact, as will be described in greater detail below, addition of the polymeric precursor to the combined gas 224 flow might actually increase the sterilization effect of the generated plasma such that improved sterilization and polymer deposition may occur simultaneously.

Figure 4:
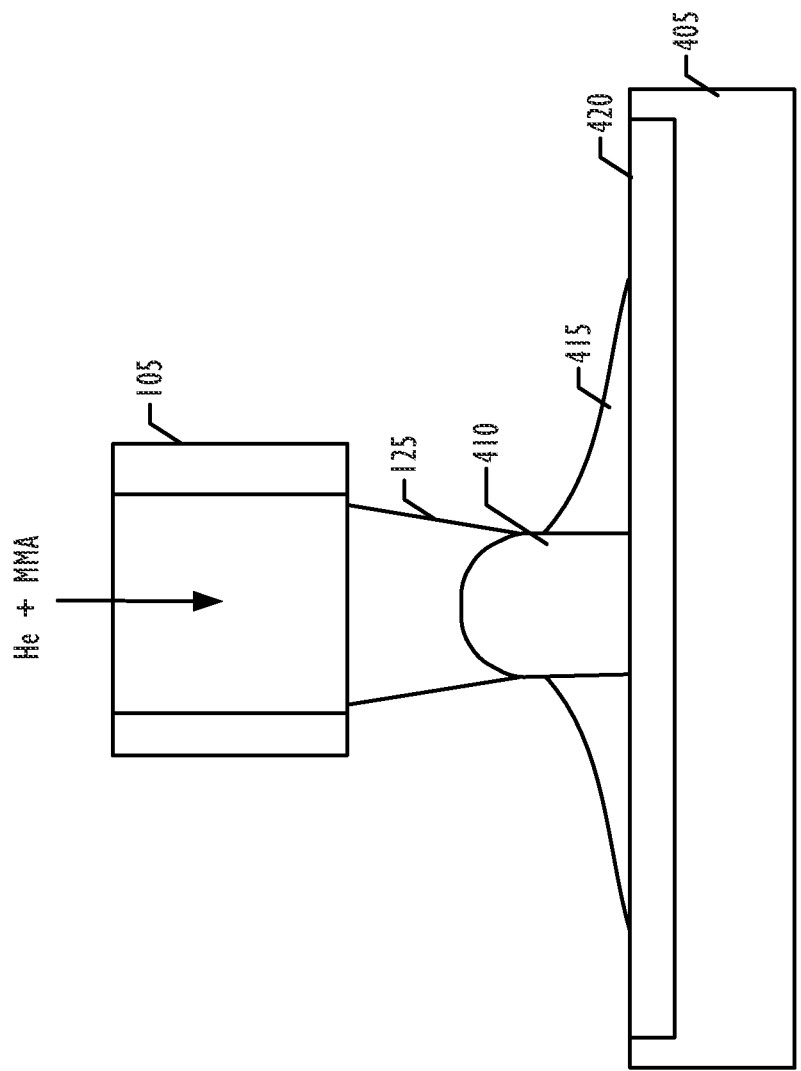
FIG. 4 illustrates the deposition of a poly-(methyl methacrylate) (PMMA) film on agar.

The beneficial effects of the above-described polymeric film bandage in sterilizing bacteria and preventing subsequent bacterial growth have been confirmed experimentally. Referring to FIG. 4, the effects of film deposition on agar 405 were evaluated. A petri dish filled with agar 405 served as the substrate 115 for the experimental analysis. The agar acts as a simplified, temperature sensitive, nutrient rich model of an actual wound. In the experimental procedure, agar 405 plates were exposed to a plasma jet 125 produced from a combined gas 224 flow composed of 2.9 slpm working gas 216 and 0.1 slpm carrier gas 218 for durations of 1 minute, 5 minutes, and 10 minutes. The carrier gas was directed through a bubbler containing MMA precursor. Additionally, agar 405 plates were exposed to a plasma jet 125 produced from a 3.0 slpm helium only flow for durations of 1 minute, 5 minutes, and 10 minutes. In each case, a 3-4 kV sinusoidal waveform having a frequency of 283 kHz was applied to the high voltage electrode 110. For the He/MMA plasma jets 125, an opaque PMMA film 410 was produced directly below the plasma jet 125 and was surrounded by a transparent PMMA film 415. Both the opaque film 110 and the transparent film 415 adhered strongly to the agar 405. In addition, the properties of the agar 405 were modified by exposure to the plasma jet 125 in a region 420.

To evaluate the sterilization and bacterial growth inhibition effects of the deposited film, a bacterium suspension of *Escherichia coli* (*E. coli*) bacteria was prepared in a liquid media having a concentration of approximately $10^9$ colony-forming units per (CFU/mL) and was plated on each of the agar 405 plates prior to exposure of the agar to the He and He/MMA plasma jets 125. After a one day incubation period, the agar 405 plates were evaluated. While a sterilized area was observed on all of the plates, the He/MMA plasma jet resulted in significantly larger sterilized areas than those treated by the He plasma jet alone. For example, the plate treated by the He/MMA plasma jet 125 for a duration of 1 minute exhibited a sterilization area similar in size to that treated by the He plasma jet 125 for a duration of 5 minutes. The relatively efficient (larger area in shorter time) sterilization of the He/MMA plasma jet 125 implies that active species generated from the MMA aid in sterilization. Therefore, in addition to the beneficial bacterial growth inhibition effects based on the deposition of a film, addition of a precursor material improves sterilization efficiency as compared to a plasma generated without the precursor addition. This beneficial effect has been observed with other precursor components as well. For example, ethyl alcohol precursor exhibited increased sterilization effects.

To further evaluate the effectiveness of the deposited PMMA film (410 and 415) as a bacterial growth inhibitor, the *E. coli* suspension was dropped on the area treated by the plasma jet 125. It is expected that the PMMA film deposited by exposure of the agar to the He/MMA plasma jet 125 should prevent access of the bacteria to the nutrient agar in the treated area, thereby inhibiting the bacterial growth in the treated area, *E. coli* growth was observed in the areas treated by the He plasma jet 125 for each of the 1 minute, 5 minute, and 10 minute treatment durations and in the area treated by the He/MMA plasma jet 125 for the 1 minute treatment durations. However, the areas exposed to the He/MMA plasma jet 125 for durations of 5 minutes and 10 minutes exhibited no additional bacterial growth. Therefore, the He/MMA plasma jet 125 both sterilizes bacteria in a treated area and results in the deposition of a PMMA film that inhibits subsequent bacterial growth in the treated area. Consequently, deposition of a PMMA film on a biological substrate in accordance with the above-described process may be utilized to form a highly sterile and conformal bandage.

Figure 5:
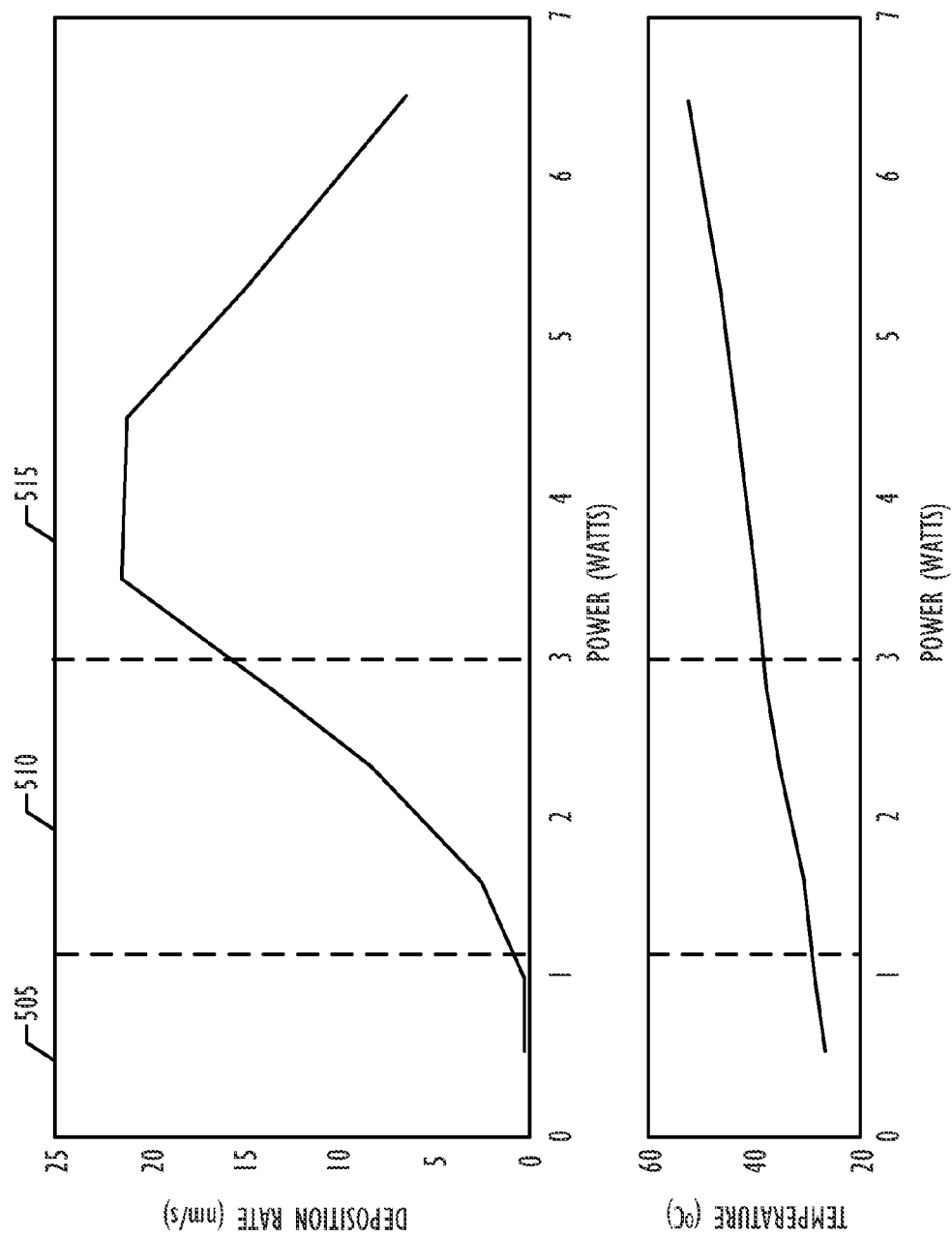
FIG. 5 is a chart that illustrates the effect of discharge power through a plasma jet on the rate of film deposition and the temperature of the substrate to which the film is being applied.

Referring to FIG. 5, in an experimental setup, voltage and current values were measured to evaluate the effect of the power dissipated through the plasma jet 125 on the temperature of the substrate and the properties of the deposited film. Voltage measurements (with respect to the ground reference) were taken at the high voltage electrode 110. Additionally, a resistor was placed in series with the substrate 115 (between the substrate 115 and the ground connection) and current measurements were obtained as a result of the voltage drop across the resistor. The voltage and current measurements were fed to an oscilloscope that calculated the average discharge power. In addition, the temperature of the substrate 115 was monitored using a thermocouple.

For several values of discharge power, the deposition process was conducted for 30 minute intervals while holding the discharge power constant (i.e., holding the magnitude of the voltage supplied to the high voltage electrode 110 constant) with working gas 216 and carrier gas 218 (through a liquid MMA solution) flow rates of 2.9 slpm and 0.1 slpm, respectively. At the end of the 30 minute interval, the thickness of the film deposited on the substrate (at the film center) was measured, and the deposition rate was calculated by dividing the film thickness by the deposition time (30 min), FIG. 5 illustrates the observed effects of discharge power on the film deposition rate as well as the temperature of the substrate.

It should initially be noted that two distinct operating modes are observed as the average discharge power is increased (as a result of increased voltage supplied to the high voltage electrode 110). A diffuse mode 505 occurs at lower values of discharge power and a concentrated mode 515 occurs at higher values of discharge power. These two modes are separated by a transition mode 510.

In the diffuse mode 505, which is observed immediately after the plasma 125 discharge is generated, the discharge color shows uniform distribution. An increase of the voltage applied to the high voltage electrode 110 results in a change in the discharge appearance. In the transition mode 510, the central part of the plasma discharge along the axial direction becomes brighter, compared with the part near the inner wall of the dielectric conduit 105. As the voltage applied to the high voltage electrode 110 is further increased, the discharge appearance contracts in the radial direction and becomes a thin bright line, representing operation in the concentrated mode 515. The discharge in the concentrated mode 515 appears to contract to a size smaller than the inner diameter of the dielectric conduit 105 and propagates along the inner wall of the dielectric conduit 105. In addition to the discharge power, the mode change phenomenon is dependent upon several other parameters, including the concentration of the precursor, the position of the high voltage electrode 110, the gap distance between the downstream end of the dielectric conduit 105 and the substrate 115, and the size and material of the dielectric conduit 105.

Referring back to FIG. 4, when the plasma jet 125 is ignited and the discharge power is less than 1 W, the discharge is observed in the diffuse mode 505. The deposition rate in the diffuse mode 505 is lower than 0.5 nanometers per second (nm/s). As discharge power is increased, the central axis of the plasma discharge starts to become brighter and the mode of operation enters the transition mode 510. The deposition rate during the transition mode 410 gradually increases as the power is increased. When the discharge power is larger than 3 W and the mode of operation enters the concentrated mode 515, a maximum PMMA deposition rate of 22 nm/s is observed. A further increase in discharge power from this point results in no significant change in the deposition rate. However, as the discharge power is increased even further, the deposition rate starts to decrease. For example, as the power is increased to 6.5 W, a deposition rate of only 7 nm/s is observed. The reduced deposition rate under high power operation is due to the fact that the plasma discharge becomes unstable in the concentrated mode 515 and shifts from the central axis to the inner wall of the dielectric conduit 105. A certain amount of MMA monomer is consumed by the formation of a film on the inner wall of the dielectric conduit 105 before landing on the substrate 115. Therefore, the film deposited on the substrate 115 is thinner at increased values of discharge power.

As is further illustrated in FIG. 4, the substrate 115 temperature increases linearly with increased discharge power. At the approximately 3.5 W discharge power corresponding to the highest film deposition rate (22 mm/s), the substrate temperature rises to a value of 39° C. These charts indicate that a high rate of deposition can be attained at temperatures that are well within a tolerable range for a temperature-sensitive substrate, such as human tissue.

Changes in the appearance of the film deposited on the substrate as a function of discharge power were also noted. In the diffuse mode 505 with 1 W discharge power, the size of the deposited PMMA film was observed to be similar to the plasma spot size. In the concentrated mode 515 with 3.5 W discharge power, the diameter of the deposited film increased. Moreover, because locally high temperature is generated by the highly concentrated plasma discharge, a yellow spot at the film center was observed. A further increase of the discharge power to 7.7 W resulted in the occurrence of a white opaque film growth at the center of the deposited film. The transparent film region surrounding the opaque film under the high power operation (7.7 W) had an even greater diameter than that observed at 3.5 W. A reduction in the gap distance between the dielectric conduit 105 and the substrate 115 from 10 mm to 3 mm resulted in an even larger circular opaque film and a larger diameter transparent film being generated at the same high power (7.7 W) operation. The variations in power and distance are thus able to affect the morphology and other characteristics of the deposited film.

While the specification has described the generation of PMMA film based on the inclusion of MMA precursor in a combined gas flow to a FE-DBD plasma generation device 100, different precursor materials that lead to different film deposits will now be described. Illustrated in Table 1 below are a few components that have been considered for inclusion as a precursor material in accordance with the above-described application of PECVD on a biological substrate.

TABLE 1

| Precursor Name | Chemical Formula | Film Deposited |
|---|---|---|
| Methyl methacrylate (MMA) | $CH_2=C(CH_3)COOCH_3$ | Poly(methyl methacrylate) (PMMA) |
| Ethylene | $H_2C=CH_2$ | Polyethylene (PE) |
| Ferrocene | $Fe(C_5H_5)_2$ | Iron |
| Copper(II) acetylacetonate (Cu(acac)$_2$) | $Cu(C_5H_7O_2)_2$ | Copper |
| Nickel(II) acetylacetonate (Ni(acac)$_2$) | $Ni(C_5H_7O_2)_2$ | Nickel |
| Cyclopentadienyl-(cycloheptatrieny)titanium(II) (CPCHT) | $(C_5H_5)Ti(C_7H_7)$ | Titanium nitride (TiN) |
| Dimethyl gold acetylacetonate (Me$_2$Au(acac)) | $(CH_3)_2Au(C_5H_7O_2)$ | Gold |
| Tetraethyl orthosilicate | $Si(OC_2H_5)_4$ | $SiO_2$ (Glass) |

The system 200 can be modified depending on the type of precursor used. For example, of the precursors listed in Table 1, some are liquids, some are gases, and some are solids at normal operating (e.g., ambient) conditions. As illustrated in FIG. 2, a bubbler can be used if the precursor is a liquid/solution, such as MMA. If the precursor is a gas, then the vessel 226 may be a gas cylinder or the like. For solid precursor, the vessel 226 may be a packed bed or sublimation chamber. Regardless of the state of the precursor material, the concentration of precursor in the carrier gas can be adjusted using flow controllers (220 and 222) and/or adjusting the temperature of the vessel 226 (e.g., bubbler or packed bed) to achieve optimum deposition rates and optimum plasma stability properties. For example, for copper(II) acetylacetonate precursor, the material is heated to approximately 50° C. to increase the sublimation rate.

As noted in Table 1, the film deposited by the PECVD process varies from polymeric materials to conductive metals as a function of the included precursor. Accordingly, a seemingly infinite number of applications for the disclosed PECVD on a biological substrate process can be imagined. For example, in medical procedures, living tissue interact with manufactured bio-materials to various degrees of complexity. Examples include electrode arrays in peripheral nerves for connections to prosthetics, artificial hip implants, inserted stents, or simple bandages. Application of the described techniques to implement PECVD on a biological substrate allows for manufacturing of these and other materials in-situ and in-vivo. For example, according to the described process, artificial implants may be bonded to bone; metallic, dielectric, or polymeric implants may be synthesized in-vivo; conductive connections to electrical devices may be synthesized; implants may be repaired in-vivo; and adhesive bandages or sutures may be applied to a wound.

It is to be understood that the above description and examples are intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

What is claimed is:

1. A method of depositing a film on a biological substrate, comprising:
    placing a dielectric conduit in the proximity of the biological substrate, the dielectric conduit having a high voltage electrode disposed about its external surface;
    directing a gas flow containing a precursor material through the interior of the dielectric conduit;
    supplying the high voltage electrode with an alternating voltage, wherein an electric field generated by a potential difference between the high voltage electrode and the biological substrate ionizes at least a portion of the gas flow causing a plasma to emanate from a downstream end of the dielectric conduit, propagate through ambient conditions, and contact the biological substrate, and wherein the plasma induces a polymerization reaction of the precursor material to form a film that is deposited on the biological substrate.

2. The method of claim 1, wherein the act of supplying the high voltage electrode with an alternating voltage comprises supplying the high voltage electrode with a sinusoidal voltage waveform.

3. The method of claim 2, wherein the sinusoidal voltage waveform has a frequency between 20 and 40 kilohertz.

4. The method of claim 1, wherein the act of directing the gas flow containing the precursor material through the interior of the dielectric conduit comprises:
    separating a supply gas flow into a working gas flow and a carrier gas flow;
    directing the carrier gas flow through a vessel that includes the precursor material; and combining the working gas flow and the carrier gas flow into the gas flow that is directed through the interior of the dielectric conduit.

5. The method of claim 4, wherein a concentration of the precursor material in the gas flow that is directed through the interior of the dielectric conduit is controlled by controlling a flow rate of the working gas flow and a flow rate of the carrier gas flow.

6. The method of claim 4, wherein the precursor material is a liquid.

7. The method of claim 6, wherein the vessel is a bubbler.

8. The method of claim 7, wherein the act of directing the carrier gas flow through the vessel comprises directing the carrier gas flow through a dip tube in the bubbler, wherein an open end of the dip tube is below a liquid level of the precursor in the bubbler.

9. The method of claim 6, wherein the carrier gas flow vaporizes at least a portion of the precursor material in the vessel.

10. The method of claim 1, wherein the precursor material is methyl methacrylate (MMA) and the film is poly-(methyl methacrylate) (PMMA).

11. The method of claim 10, wherein the biological substrate is human skin tissue that contains a wound.

12. The method of claim 1, wherein the alternating voltage has an arbitrary programmed waveform.

13. An apparatus for depositing a film on a biological substrate, comprising:

a gas flow system for generating a combined gas flow that includes a precursor material; and a floating electrode dielectric barrier discharge device, comprising:

a dielectric conduit having an internal portion through which the combined gas flow is directed;

a high voltage electrode disposed about an external surface of the dielectric conduit; and a power supply configured to supply the high voltage electrode with an alternating voltage, wherein an electric field generated by a potential difference between the high voltage electrode and the biological substrate ionizes at least a portion of the combined gas flow causing a plasma to emanate from a downstream end of the dielectric conduit and to contact the biological substrate, and wherein the plasma induces a polymerization reaction of the precursor material to form a film that is deposited on the biological substrate.

14. The apparatus of claim 13, wherein the gas flow system comprises a working gas flow path, a carrier gas flow path, and a combined gas flow path.

15. The apparatus of claim 14, wherein a supply gas flow is separated into a working gas flow through the working gas flow path and a carrier gas flow through the carrier gas flow path.

16. The apparatus of claim 15, wherein the carrier gas flow path directs the carrier gas flow through a vessel that includes the precursor material.

17. The apparatus of claim 16, wherein the working gas flow path comprises a working gas flow controller and the carrier gas flow path comprises a carrier gas flow controller.

18. The apparatus of claim 17, wherein a concentration of the precursor material in the combined gas flow is maintained by controlling a flow rate of the carrier gas flow using the carrier gas flow controller and by controlling a flow rate of the working gas flow using the working gas flow controller.

19. The apparatus of claim 13, wherein the film is a metallic film.

20. The apparatus of claim 13, wherein the precursor material is a solid.

21. The apparatus of claim 13, wherein the precursor material is gaseous.

22. The apparatus of claim 13, wherein the precursor material increases the sterilization efficiency of the plasma as compared to plasma generated without the precursor material.

23. The apparatus of claim 13, wherein the biological substrate is human skin tissue and the film sterilizes a wound in the skin tissue and prevents an infection of the wound.

* * * * *